US00RE47439E

(19) United States
(12) Reissued Patent
Gazda et al.

(10) Patent Number: US RE47,439 E
(45) Date of Reissued Patent: Jun. 18, 2019

(54) METHOD FOR MANUFACTURE OF MACROBEADS

(71) Applicant: THE ROGOSIN INSTITUTE, New York, NY (US)

(72) Inventors: Lawrence Gazda, Xenia, OH (US); Melissa Laramore, Xenia, OH (US); Timothy Hamilton, Xenia, OH (US); Barry Smith, New York, NY (US)

(73) Assignee: THE ROGOSIN INSTITUTE, New York, NY (US)

(21) Appl. No.: 15/226,341

(22) Filed: Aug. 2, 2016

Related U.S. Patent Documents

Reissue of:
(64) Patent No.: 9,090,866
Issued: Jul. 28, 2015
Appl. No.: 13/754,076
Filed: Jan. 30, 2013

U.S. Applications:
(60) Provisional application No. 61/592,949, filed on Jan. 31, 2012.

(51) Int. Cl.
*C12N 5/00* (2006.01)
*B25J 15/06* (2006.01)

(52) U.S. Cl.
CPC ..... *C12N 5/0012* (2013.01); *B25J 15/0616* (2013.01)

(58) Field of Classification Search
CPC ..... C12N 5/0012
See application file for complete search history.

(56) References Cited

U.S. PATENT DOCUMENTS

| | | | | |
|---|---|---|---|---|
| 5,643,569 | A | 7/1997 | Jain et al. | |
| 5,888,497 | A | 3/1999 | Jain et al. | |
| 6,224,912 | B1 | 5/2001 | Asina et al. | |
| 6,303,151 | B1 | 10/2001 | Asina et al. | |
| 6,497,155 | B1 | 12/2002 | Feygin et al. | |
| 6,558,665 | B1 | 5/2003 | Cohen et al. | |
| 6,808,705 | B2 | 10/2004 | Asina et al. | |
| 6,818,230 | B2 | 11/2004 | Asina et al. | |
| 7,358,098 | B2 | 4/2008 | Noda et al. | |
| RE40,555 | E | 10/2008 | Jain et al. | |
| D625,429 | S | 10/2010 | Link et al. | |
| 7,838,291 | B2 | 11/2010 | Conn et al. | |
| 8,015,887 | B2 | 9/2011 | Ayliffe et al. | |
| 2001/0015372 | A1 | 8/2001 | Yamamoto et al. | |
| 2003/0012699 | A1* | 1/2003 | Moore et al. | 422/100 |
| 2005/0053586 | A1 | 3/2005 | Conn et al. | |
| 2007/0069408 | A1 | 3/2007 | Cheng et al. | |
| 2007/0071732 | A1 | 3/2007 | Gazda | C12N 5/0677 424/93.7 |
| 2008/0202631 | A1 | 8/2008 | Loewenthal et al. | |
| 2010/0317113 | A1* | 12/2010 | Deshayes et al. | 435/396 |
| 2012/0085181 | A1 | 4/2012 | Etzold et al. | |
| 2013/0277872 | A1 | 10/2013 | Vincze et al. | |
| 2014/0055568 | A1 | 2/2014 | Etzold et al. | |

FOREIGN PATENT DOCUMENTS

| | | | |
|---|---|---|---|
| DE | 102010040681 | A1 | 3/2012 |
| DE | 102010040684 | A1 | 3/2012 |
| EP | 1522340 | A1 | 4/2005 |

OTHER PUBLICATIONS

Sigma. Product information, agarose. Oct. 21, 1996.*
Nussinovitch, A., Bead Formation, Strengthening, and Modification, Polymer Macro- and Micro-Gel Beads: Fundamentals and Applications, 2010, vol. XXV, pp. 27-52.*
Gradient definition (physics), Oxford Dictionary (American English) (US), Accessed at http://www.oxforddictionaries.com/us/definition/american_english/gradient, on Mar. 10, 2015.*
International Search Report from PCT/US2013/023802 dated May 9, 2413 (4 pages).

* cited by examiner

*Primary Examiner* — Bruce R Campell
(74) *Attorney, Agent, or Firm* — Abelman, Frayne & Schwab

(57) ABSTRACT

The invention relates to an improved method for making agarose coated, agarose beads which contain cells. The method which is preferably automated, involves placing manufactured beads in a sample of mineral oil at a temperature gradient, such that the temperature drops as the bead moves through the oil. Preferably, a "trumpet tool" and a "straw tool" are employed in the method.

17 Claims, 8 Drawing Sheets

METHOD FOR MANUFACTURE OF MACROBEADS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application claims priority from U.S. Provisional Application No. 61/592,949 filed Jan. 31, 2012, incorporated by reference in its entirety.

FIELD OF THE INVENTION

This invention relates to improved methods for making a composition of matter which comprises cells, secretory cells in particular, entrapped in a permeable bead or other structure, which is then coated with agarose. The bead may comprise or consist of agarose. Litex agarose is especially preferred for the beads.

BACKGROUND AND PRIOR ART

The manufacture of compositions of matter which contain viable cells, entrapped in permeable media, has been shown to be important in various fields, such as diabetes therapy, cancer treatment, and stem cell maintenance. In this regard, see, e.g., Reissue 40,555; U.S. Pat. Nos. 7,838,291; 6,818,230; 6,808,705; 6,303,151; 6,224,912; 5,888,497; and 5,643,569, and published patent application 2007/0071732, all of which are incorporated by reference in their entirety.

The processes for making these compositions of matter, hereafter referred to as "encapsulates," has been essentially the same, regardless of the type of cell used. After isolation or securing of the cells of interest, these are suspended in an aqueous solution of an agent such as agarose, collagen, or combinations of such, or placed on a material such as gelatin sponge. When aqueous solutions are used, semi-solid beads containing the cells of interest are formed by placing the suspension in mineral oil. If gelatin sponge is used, the product, containing the cells, is rolled into a sphere, after which agarose is poured onto it, to form a bead.

The beads are then contacted to a solution of agarose, in, e.g., a Teflon spoon. The beads roll in the mixture, to form what are referred to in the art cited supra as agarose-coated macrobeads.

The initial teachings as shown by, e.g., RE 40,555 and U.S. Pat. No. 5,888,497 which teach encapsulation of secretory cells, such insulin producing islets and cancer cells, have been followed by improvements, including the encapsulation of stem cells, as shown by U.S. Pat. No. 7,838,291 and via improvements in materials used, as seen in, e.g., published patent application 2007/0071732; however, there is an ongoing need to improve the methodology for making these useful materials.

One improvement, which is very desirable in this field, is the ability to automate what is a manual process.

In the course of automating the process of manufacture, the inventors have developed special tools, which facilitate the manufacturing process. In addition, they have found that in finishing the process via placing the macrobeads in a vessel of mineral oil at a temperature gradient, one can produce macrobeads with more uniform shape and even texture than was believed possible.

How this is accomplished will be seen in the disclosure, which follows.

DETAILED DESCRIPTION OF PREFERRED EMBODIMENTS

Reference is made to the U.S. Patents cited supra, all of which describe detailed manual methodologies for making macrobeads, which contain different types of cells, such as secretory cells as defined therein. The invention described herein modifies those methods by replacing the final step of contacting the agarose coated, agarose beads with mineral oil in a spoon or on a Teflon surface, with a vessel containing mineral oil kept at a temperature gradient, as described infra.

Macrobeads such as are described in these patents may also be made robotically or via automation. One such approach is described herein.

Figure 1:
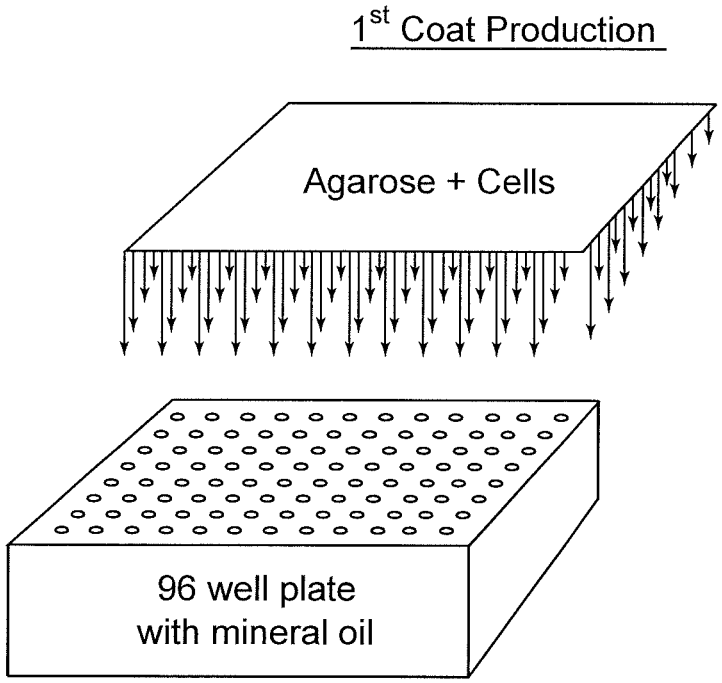
FIG. 1 shows the automated dispensing of cells and agarose into a multiwell array which contains mineral oil.

In one embodiment, as in depicted FIG. 1, a robotic dispenser, such as an array of pipettes, dispenses secretory cells into a multiple well plate, such as a standard 96 well plate. Molten agarose is then added to the wells. The cells and molten agarose are then transferred via, e.g., automated means such as a multi-pipette array, to mineral oil containing means such as single well or multiwell containers, such as 96 well plates, to form beads.

The beads are then removed from the wells, preferably via the use of a so-called "trumpet tool," depicted in FIGS. "2a-c and 3." The trumpet tool, as is elaborated upon infra, is designed so as not to disrupt the surface of the bead.

In a further embodiment, an exit means is provided at the bottom of the well, by which the beads escape the well and may be used in the steps which follow. In a still further embodiment, the beads resulting from the process discussed supra, may be transferred to the top of the mineral oil via automated means, such as a moveable platform, and also removed from the mineral oil containing means, via automated systems.

Figure 4A:
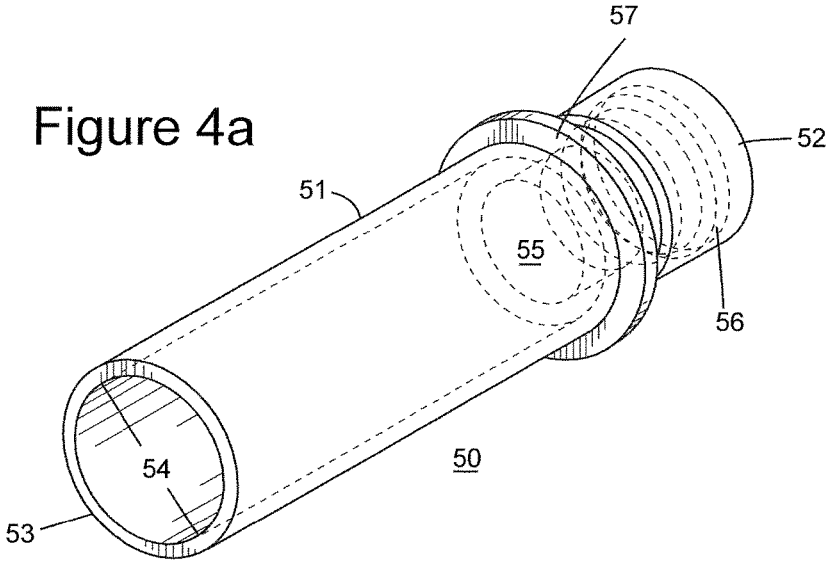
FIGS. 4a and 4b show different embodiments of the straw tool invention.
Figure 4B:
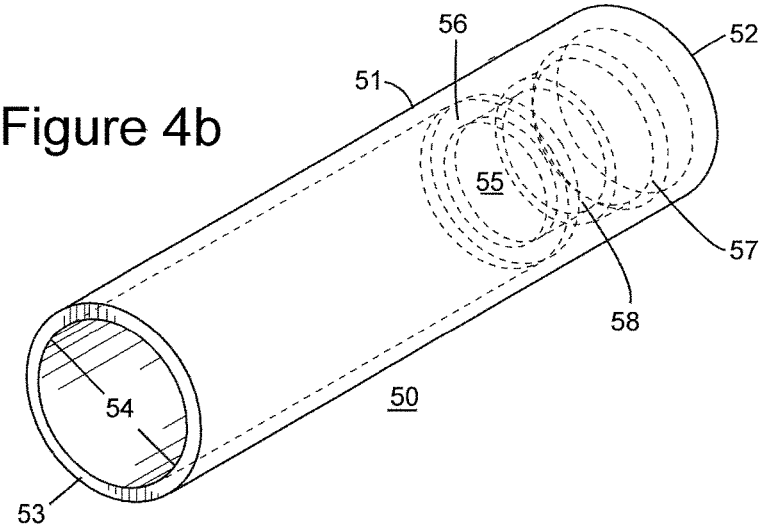

Following pick up by the trumpet tool, or passage via the exit means, and removal of any adherent mineral oil by means of rinsing with an appropriate solution, such as a balanced salt solution, the beads are placed in wells containing new, warmed agarose. Following this, the beads are removed together with the warm agarose, preferably using a so-called "straw tool," as shown in FIGS. 4a and 4b using mild suction, and are dispensed to vessels containing mineral oil at a controlled temperature gradient.

The vessel containing the mineral oil may be, e.g., a test tube, cuvette, beaker, or any other object that is suitable, although test tubes and cuvettes, of various sizes are preferred. The material used to make these containers, i.e., the test tubes, cuvettes, etc., may vary. Glass is especially preferred, although other materials, such as those coated with a substance to provide a hydrophilic layer, may be used.

The temperature gradient in the vessel may be maintained by any method known to the art. Key is that the temperature of the mineral oil be higher at the top of the vessel than at the bottom thereof. The temperature and amount of gradient will vary based on, e.g., the length of the vessel, the type of cell encapsulated, the type of agarose used, and so forth. The factors which are important to setting these values include, e.g., temperatures at which the encapsulated cells are viable, temperatures at which the agarose employed will solidify, and so forth. The temperature at the start of the gradient is preferably from 20° C. to 80° C., more preferably from 20° C. to 50° C., and even more preferably, from 20° C. to 40° C. Ideally, the starting temperature is from about 20° C. to about 25° C. The temperature at the bottom of the vessel may also vary, ranging from, e.g., 0° C. to −10° C., more preferably 0° C. to −8° C., and most preferably from about 0° C. to about −2° C. The total differential between the highest and lowest temperatures is preferably from 20° C. to 50° C., more preferably from about 20° C. to about 30° C.

The figures which area part of this application will amplify upon the preceding description.

FIG. 1 shows how both the cells and the agarose are dispensed into wells of plates. Following removal of the mineral oil via, e.g., washing or aspiration, or via the exit means discussed supra, the "trumpet tool" referred to supra, and as is shown in FIGS. 2a-2c and 3 is inserted into the well, so as to remove the beads with entrapped cells. This trumpet tool has a vacuum source attached at one end, which does not disrupt the surface of the bead so as to facilitate its removal.

Figure 5:
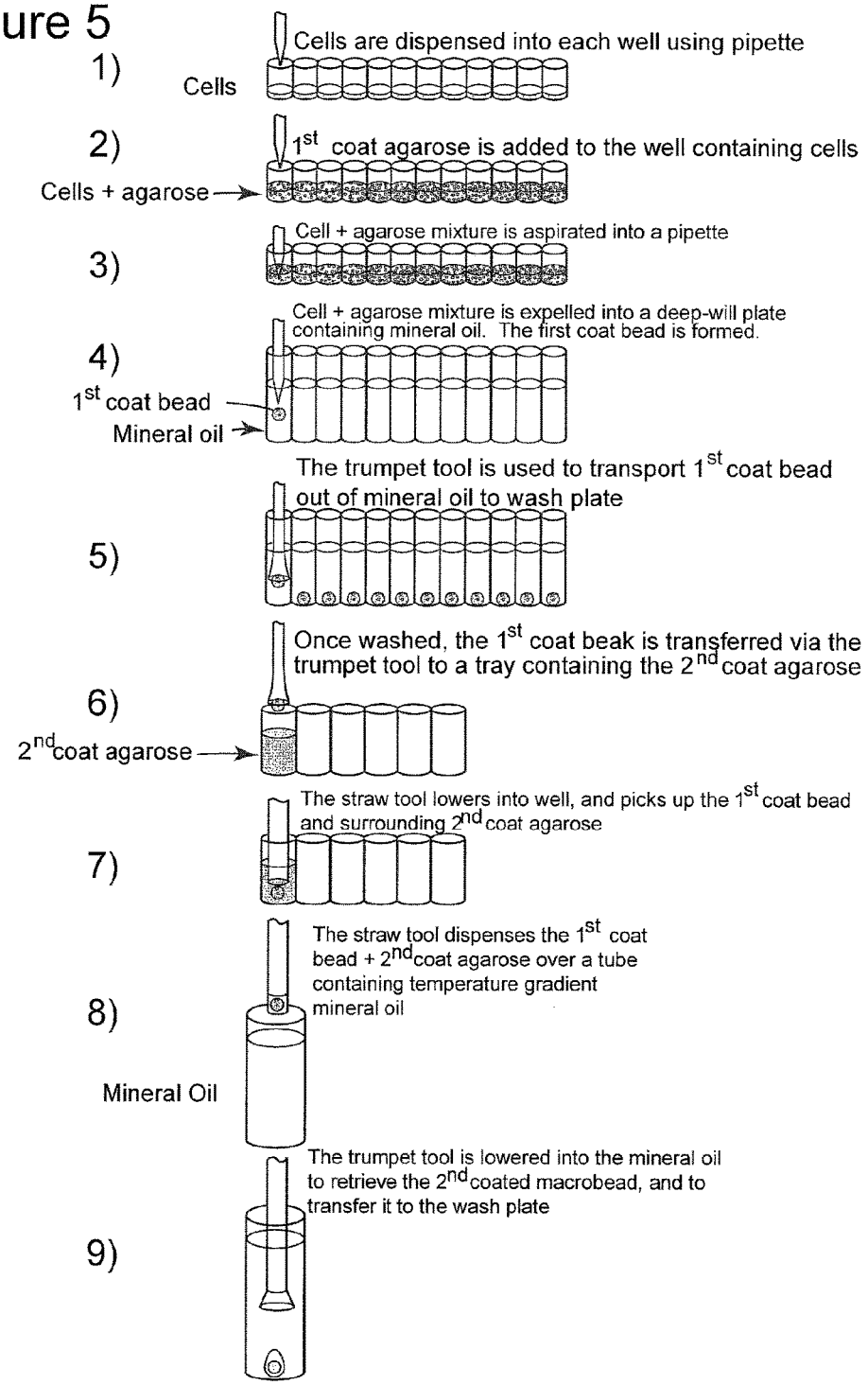
FIG. 5 depicts a summary of the process of the invention.

The bead consisting of one layer of agarose and the cells is deposited via the so-called "trumpet tool" into a new well, filled with heated agarose which serves as the second layer, or coating of agarose. The bead is removed together with the warm agarose, preferably by using a "straw tool," such as one of those shown in FIGS. 4a and 4b, preferably with the aid of mild suction, and the bead is dispensed to a vessel containing the temperature gradient mineral oil. The temperature gradient may be maintained by, e.g., the device shown in FIG. 5, but the skilled artisan will be familiar with other options. When the macrobead has traversed the vessel and has reached the bottom an elongated form of the trumpet tool may be used, with suction, to remove the macrobeads for washing in medium, or as noted, supra, an exit means for removal of the bead may be employed. At this point, the macrobeads are ready for use, although in different situations it may be preferable to permit the cells to proliferate and/or mature within the beads until a sufficient number are present or until a specific product is expressed by the cells. This time period could range from, e.g., a week to several months.

Referring now to the figures of the claimed invention, FIGS. 2a, 2b, 2c, and 3 show different views of devices in accordance with the invention, the so called "trumpet tool."

Figure 2A:
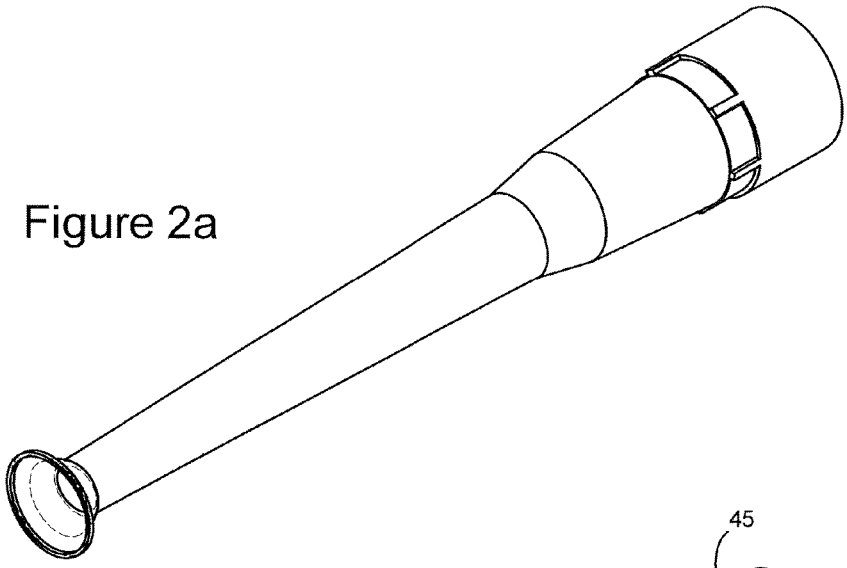
FIGS. 2a-2c present different views of a preferred embodiment of the "trumpet tool" of the invention.

Referring to FIG. 2a, a trumpet tool 40 is shown. The description of the tool as a "trumpet tool" comes from the resemblance of negative conical section 41 to a trumpet. At one end, a negative conical segment 41 is provided, with a rim 42 attached to the conical end 41. The conical end 41 connects to a hollow, longitudinal section 43 which is adapted for passage of a fluid therethrough, such as air.

As FIG. 2a shows, the hollow longitudinal section 43 runs along the entirety of the device. One can see collar means 44 positioned about ⅔ to ¾ of the way along the length of the trumpet tool, relative to the negative conical end. The collar means 44, as well as several other features described herein, are artifacts of the manufacturing process and do not impact the functioning of the device.

Collar means 44, however, marks the point at which the longitudinal means expands its circumference. The portion of the device represented by 45 corresponds to a coupling end which, in operation, connects the tool to a source of fluid, e.g., air, such as a vacuum. Connection aperture 46 has the widest circumference of any part of the device and acts to complete connection to, e.g., a vacuum means. Internal structures, such as those exhibited in FIG. 2c, are provided to facilitate attachment of vacuum means. These structures may vary, based upon the apparatus being used.

One observes a ridge means 47 in the device, as well as a series of evenly spaced projections 48a, b, and c, all of which are, as with collar means 44, artifacts of manufacturing; however, these projections also serve to help hold their associated tools in place in, e.g., a dispensing rack.

Figure 2B:
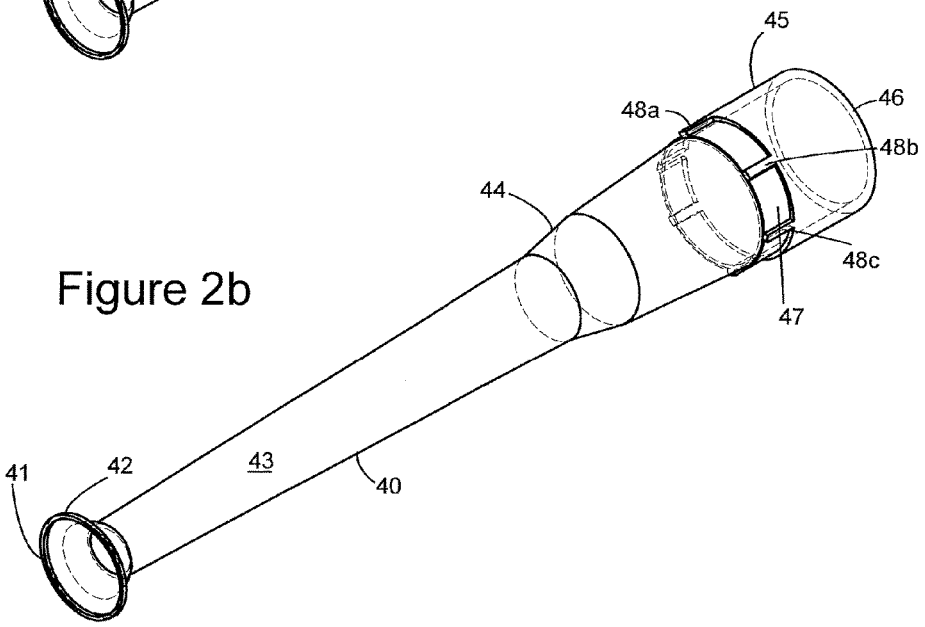
Figure 2C:
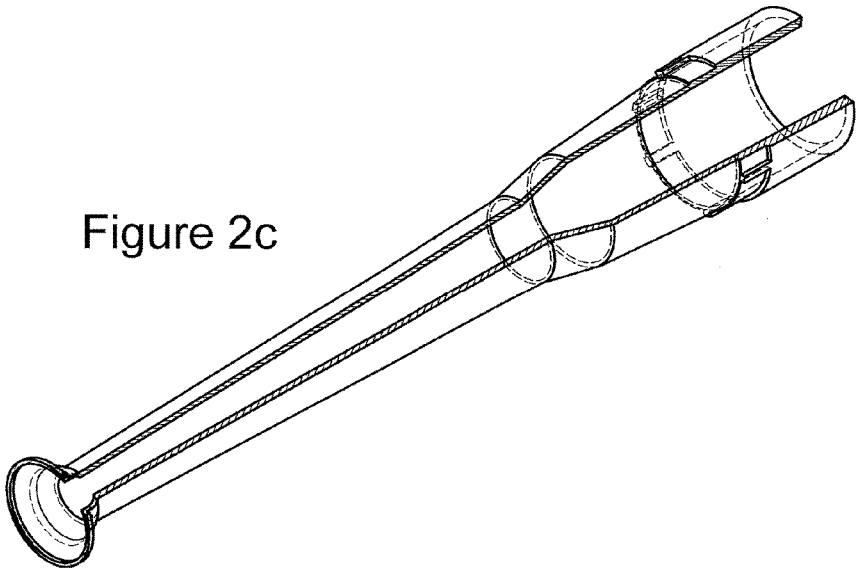

The interior of the device can be seen in both FIGS. 2b and 2c, where it can be seen that in fact the device is hollow along its entire length. The view of negative conical segment in FIG. 2c shows in greater detail how it tapers to a point where the circumference is slightly smaller than an object it is designed to engage, e.g., a bead.

In operation, the device 40 is connected via connection end 46 to, e.g., a vacuum pump means, and is positioned, vertically over the object to be removed, such as a bead. The vacuum pump means (not shown), removes any air within the tool, and permits uptake of the bead, e.g., via controlling the force of the suction created by the vacuum, the configuration of the negative conical end 41 permits removal of a bead, such as a semi-soft agarose bead, from one position, and movement to another, such as a solution of coating agarose. At that point, the vacuum pressure is changed via, e.g., providing air to longitudinal means 45, which acts to expel the bead into the agarose solution from conical end 41 without any changes to the configuration of the bead.

Figure 3:
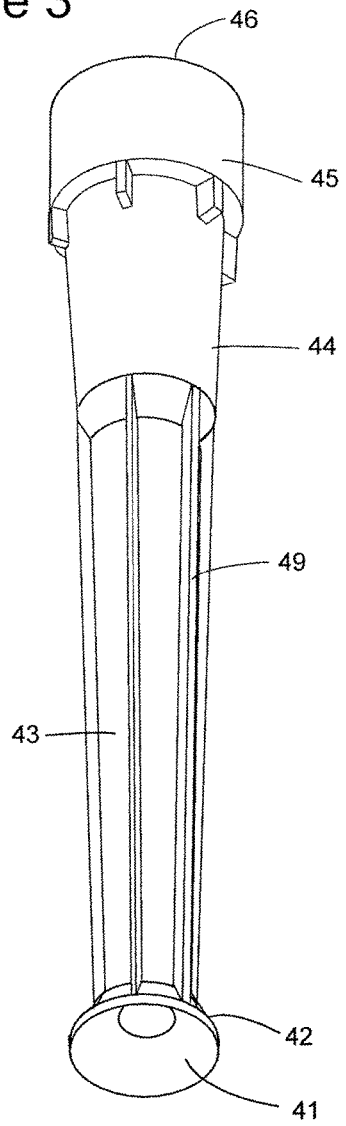
FIG. 3 shows a second embodiment of the trumpet tool.

FIG. 3 shows another embodiment of the device of FIGS. 2a-2c. This device, prepared via a different manufacturing means than the embodiment of FIGS. 2a-2c, exhibits ridge means along the longitudinal section 43. Also, it will be noted that there are variations in the collar means, as well as in the ridge means 47 and 48a-c. The negative conical end 41 and its rim, as well as the coupling end 45 and connecting aperture, however, function in the same way as the comparable structures of FIGS. 2a-2c.

FIGS. 4a and 4b depict embodiments of a device known hereafter as the "straw tool." Referring now to FIG. 4a a straw tool 50 is shown. The tool exhibits essentially cylindrical geometry along a hollow longitudinal axis 51, a coupling end 52, and a receiving end 53.

The straw tool includes a recessed space 54, which extends along the longitudinal axis 51, opening at receiving end 53.

The receiving space 54 extends along the longitudinal axis and, which adjoins a canal section 55, which can have a smaller diameter than the receiving space. This canal section 55 joins connecting means 52, and the combination of "52," "54" and "55" form a working channel which accepts changes in pressure of a fluid, such as air or another gas. In operation, connecting means 52, is coupled to a device capable of changing pressure of a fluid in the straw tool, such as an air pump. The straw tool is then placed over an object, such as a bead, and upon the change in pressure, the bead is removed by the straw tool. It should be noted that the diameter of the opening at receiving end 53 is large enough to pick up the object, e.g., the bead and to permit the bead to move vertically in the longitudinal cavity of the tool. Once the bead is moved to the desired location, a second change of pressure causes the bead to drop, and permit re-use of the straw tool.

FIGS. 4a and 4b differ in that configurations of the connecting means 52 are different; however, the difference in configurations results from manufacturing processes and does not impact the operation of the device.

In each device, broken lines indicate adaptation of the straw tool for reception of a vacuum connecting means of choice. A recessed channel 56 is depicted, which is capable of accepting a connection means, such as an expandable O-ring. Also a feature of the device is a means 57, for impeding progress of a pipette. This "pipette shelf" stops passage of a pipette or other delivery means for the fluid, e.g., air.

The examples which follow should be taken as exemplary, but not limitative, of the invention as it is described herein.

Example 1

Powdered agarose (Litex HSB-LV) was dissolved in minimal essential medium to a concentration of either 0.8% or 4.5% (w/v), and then autoclaved at 121° C., for 20 minutes. This produced viscous molten solutions. The agarose solutions were cooled and maintained at 51-53° C., or 61-63° C., respectively.

A total of 150,000 RENCA (renal cancer) cells were added to a well, after which 0.25 ml of the 0.8% agarose solution was added to form a suspension, and this cell/agarose suspension was then dispensed into either room temperature mineral oil in a plastic bowl, or into a deep well 96 plastic plate, previously filled with room temperature mineral oil.

RENCA cell containing agarose macrobeads formed, as round beads with smooth surfaces, and evenly distributed cells. The mineral oil was then aspirated away from the macrobeads, and the macrobeads were washed with RPMI cell culture medium.

The coating for the macrobead used the 4.5% w/v solution. The agarose for the coating was same type as was used for the beads; however, it should be noted that they can differ.

To carry out the manual mode for preparing the beads, the beads prepared supra, were rolled in a plastic spoon which contained 1.0 ml of the 4.5% agarose, which had been maintained at 61-63° C., after which they were dropped into room temperature mineral oil.

In the method of the invention, the coating material was maintained at 61-63° C., and was transferred to a 24 well plate. The "trumpet tool" shown in FIG. 2a and discussed, supra, was then used to remove the beads from the room temperature mineral oil and to place them into the second coat, agarose solution following washing of the beads to remove the mineral oil. A straw tool, depicted in FIG. 4a, was used together with gentle suction, to remove the beads, together with 0.5 ml of agarose to a vessel containing mineral oil maintained at a temperature gradient.

Macrobeads were dispensed from the straw tool, into the top of the mineral oil gradient, which was maintained at varying temperatures, as discussed infra. As the macrobead descended through the mineral oil, the coating solidified on the bead forming a sphere. The temperature of the mineral oil decreased from the top to the bottom of the vessel, to a low temperature at the bottom, also as described infra. The agarose/agarose macrobeads were then removed from the vessel using the trumpet tool of FIG. 2a and were then washed in media. The resulting macrobeads were then ready for routine tissue culture.

Example 2

A series of different experiments, using the temperature gradient described, supra were used.

| Experiment | Top Temperature | Bottom Temperature |
|---|---|---|
| Control | RT (Room Temperature) | RT (Room Temperature) |
| 1 | 25° C. | −2° C. |
| 2 | 30° C. | −2° C. |
| 3 | 40° C. | −2° C. |
| 4 | RT | RT |
| 5 | 50° C. | −1.8° C. |
| 6 | 60° C. | −1.6° C. |
| 7 | RT | RT |
| 8 | 70° C. | 0° C. |
| 9 | 25° C. | −2° C. |

After beads were recovered and washed, as discussed, supra, they were tested for metabolic activity. This evaluation was carried out using a standard MTT assay, which is well known in the art. Metabolic activity was determined at day =0 for non-encapsulated cells, and at 7 days post-production for the encapsulates. The results are summarized below.

| | Experiment | | | | | | | | | |
|---|---|---|---|---|---|---|---|---|---|---|
| | Control | 1 | 2 | 3 | 4 | 5 | 6 | 7 | 8 | 9 |
| Free Cells | 0.603 | 0.682 | 0.682 | 0.682 | 0.669 | 0.723 | 0.723 | 0.517 | 0.686 | 0.686 |
| Encapsulates | 0.507 | 0.411 | 0.299 | 0.279 | 0.261 | 0.182 | 0.173 | 0.448 | 0.167 | 0.415 |

The results indicate that while the encapsulated cells survived regardless of the starting temperature when dropped into the gradient, metabolic activity was inversely proportional to the temperature at which the gradient began, i.e., the higher the temperature, the lower the resulting metabolic activity.

Example 3

Given that the optimal starting temperature of the mineral oil gradient was established to be about 25° C., and the ending temperature about −2° C., this was used in a set of experiments to determine metabolic activity, and tumor inhibitory capacity.

Metabolic activity was determined in the same manner set forth supra.

Tumor inhibitory activity was determined by seeding RENCA cells into 6 well plates (15,000 cells/well) in either 4 ml of fresh culture medium, or the same amount of culture medium taken from cultures of the encapsulates, following 5 days of culture. The free RENCA cells were cultured in the medium, for 5 days at 37° C. and a 5% $CO_2$ atmosphere. The RENCA cells were then fixed with methanol, stained with 0.33% (w/v)P neutral red, and absorbance was determined at 540 nm, using 630 nm as a reference wavelength. Inhibition was defined as the percent difference in $Abs_{540\ nm-630\ nm}$ between treated, and fresh media.

The results that follow present metabolic activity data. "Free cell" refers to RENCA cells which were not treated with agarose at all, while "1st coat" refers to uncoated beads.

| Age (days) | Type | Control | 1 | Control 2 | 2 | Control 3 | 3 | 4 | Control 4 | 5 | 6 | Control 5 | 7 |
|---|---|---|---|---|---|---|---|---|---|---|---|---|---|
| 0 | Free Cell | 0.768 | 0.530 | 0.378 | 0.462 | 0.481 | 0.532 | 0.532 | 0.384 | 0.518 | 0.518 | 0.530 | 0.553 |
| 1 | 1st coat | 0.926 | 1.209 | 0.912 | 1.279 | 1.056 | 1.120 | 1.120 | 1.129 | 1.002 | 1.002 | 1.157 | 1.711 |
| 7 | 1 week | 0.247 | 0.260 | 0.332 | 0.143 | 0.739 | 0.801 | 0.710 | 0.409 | 0.390 | 0.227 | 1.330 | 0.697 |
| 21 | 3 week | 0.201 | 0.351 | 0.328 | 0.258 | 0.555 | 0.560 | 0.770 | 0.462 | 0.531 | 0.380 | 0.977 | 0.555 |
| 35 | 5 week | 0.647 | n/a | 0.856 | n/a | 1.156 | n/a | 1.092 | 1.141 | n/a | n/a | 1.447 | n/a |
| 49 | 7 week | 1.080 | n/a | 1.236 | n/a | 1.324 | n/a | 1.066 | 1.215 | n/a | n/a | 1.926 | n/a |
| 84 | 12 week | 1.025 | n/a | 1.548 | n/a | 1.623 | n/a | 1.095 | 1.725 | n/a | n/a | 1.886 | n/a |
| 112 | 16 week | 1.652 | n/a | 2.440 | n/a | 2.247 | n/a | 1.128 | 1.872 | n/a | n/a | n/a | n/a |

In the table which follows, the tumor inhibitory capacity was determined:

| Age (days) | Type | Control | 1 | Control | 2 | Control | 3 | 4 | Control | 5 | Control | 6 |
|---|---|---|---|---|---|---|---|---|---|---|---|---|
| 35 | % | 29.99% | 29.80% | 12.78% | −11.23% | 11.10% | 7.54% | 17.37% | 23.97% | 26.20% | 33.85% | 33.28% |
| 49 | % | 23.62% | 33.53% | 26.15% | 33.98% | 32.70% | 29.63% | 29.63% | 34.54% | 40.90% | n/a | n/a |
| 84 | % | 33.10% | 45.69% | 23.41% | 33.93% | 43.20% | 56.02% | 56.09% | n/a | n/a | n/a | n/a |
| 112 | % | 50.19% | 55.66% | 42.21% | 46.03% | 55.28% | 44.84% | n/a | n/a | n/a | n/a | n/a |

The results indicate that the agarose beads produced in accordance with the invention are equivalent in all relevant respects to manually produced beads.

Example 4

Beads were produced in accordance with the invention as described supra, and the manual method as represented via the cited prior art. Over a period of 7 months, ten beads were selected, at random to determine their diameters. The results, presented in the table which follows, shows that beads produced in accordance with the invention have a more consistent diameter, and hence a more consistent coating.

| | Automated: Diameter (in) | Manual: Diameter (in) |
|---|---|---|
| January | 0.352 | 0.350 |
| | 0.363 | 0.347 |
| | 0.364 | 0.347 |
| | 0.354 | 0.353 |
| | 0.350 | 0.346 |
| | 0.347 | 0.348 |
| | 0.355 | 0.351 |
| | 0.348 | 0.350 |
| | 0.353 | 0.352 |
| | 0.347 | 0.350 |
| February | 0.350 | 0.350 |
| | 0.354 | 0.328 |
| | 0.351 | 0.327 |
| | 0.354 | 0.326 |
| | 0.361 | 0.324 |
| | 0.353 | 0.332 |
| | 0.355 | 0.325 |
| | 0.362 | 0.328 |
| | 0.353 | 0.321 |
| | 0.348 | 0.316 |
| March | 0.335 | 0.322 |
| | 0.354 | 0.317 |
| | 0.357 | 0.308 |
| | 0.364 | 0.347 |
| | 0.356 | 0.331 |
| | 0.349 | 0.313 |
| | 0.351 | 0.346 |
| | 0.334 | 0.333 |
| | 0.358 | 0.329 |
| | 0.352 | 0.307 |
| April | 0.332 | 0.344 |
| | 0.342 | 0.331 |
| | 0.345 | 0.324 |
| | 0.334 | 0.334 |
| | 0.351 | 0.344 |
| | 0.375 | 0.346 |
| | 0.345 | 0.339 |
| | 0.343 | 0.319 |
| | 0.368 | 0.339 |
| | 0.346 | 0.331 |
| May | 0.368 | 0.335 |
| | 0.344 | 0.332 |
| | 0.349 | 0.322 |
| | 0.333 | 0.317 |
| | 0.346 | 0.315 |
| | 0.337 | 0.316 |
| | 0.341 | 0.318 |
| | 0.329 | 0.347 |
| | 0.347 | 0.317 |
| | 0.329 | 0.332 |
| June | 0.370 | 0.330 |
| | 0.318 | 0.357 |
| | 0.350 | 0.346 |
| | 0.350 | 0.343 |
| | 0.351 | 0.347 |
| | 0.347 | 0.345 |
| | 0.353 | 0.336 |
| | 0.347 | 0.344 |
| | 0.347 | 0.318 |
| | 0.363 | 0.332 |
| July | 0.341 | 0.347 |
| | 0.349 | 0.343 |
| | 0.350 | 0.345 |
| | 0.346 | 0.326 |
| | 0.366 | 0.324 |

-continued

| | | |
|---|---|---|
| | 0.361 | 0.342 |
| | 0.362 | 0.357 |
| | 0.348 | 0.321 |
| | 0.351 | 0.314 |
| | 0.369 | 0.335 |
| Parameter | Auto | Manual |
| Mean | 0.350386 | 0.3339714 |
| Standard Error | 0.001267 | 0.0015674 |
| Median | 0.35 | 0.3325 |
| Mode | 0.347 | 0.347 |
| Standard Deviation | 0.010601 | 0.0131137 |
| Sample Variance | 0.000112 | 0.000172 |
| Kurtosis | 0.697026 | −1.117773 |
| Skewness | −0.30036 | −0.151897 |
| Range | 0.057 | 0.05 |
| Minimum | 0.318 | 0.307 |
| Maximum | 0.375 | 0.357 |
| Sum | 24.527 | 23.378 |
| Count | 70 | 70 |

Also, upon examination, it was found that the process of the invention resulted in reduced cellular contamination. To elaborate, it has been found that when beads are prepared in accordance with the manual method of the prior art, there is an issue with cells that do not become fully encapsulated. When the cells are cancer cells, plaques, or tumor colonies form, and the beads in the culture with them must be discarded due to the contamination.

Over an 8-month period, 56 batches of beads were made manually, each batch containing a number of Petri dish cultures. At least one culture was contaminated in each batch. In contrast, 62 batches were prepared over the same period using the method of the invention. Only 12 of those 62 batches showed any type of contamination.

Example 5

The following example details the production of three different groups of agarose coated, agarose bead containing islets.

Islets were prepared from animals over two years of age and with a history of multiple parities.

The pancreases of the animals were perfused with a collagenase/neutral protease (either Collagenase P, at 1.0 g/L, or Liberase MTF/Thermolysin, at 7.5 U/g pancreas), and 0.01 g/L DNase I, or 2.5 mg/pancreas pulmozyme solution, prepared in either Hanks Balanced Salt Solution (GBSS) or Cold Storage Purification Stock Solution.

After quantification, islets were separated into 2000 IEQ aliquots, before being resuspended in a 0.5 ml solution of one of 1.5% Seakem Gold ("SG" hereafter, 0.8% SG, or 0.8% Litex ("Li" hereafter). An "IEQ" as used herein means an islet having a diameter of 150 μm. Hence, an islet with a diameter of 300 μm is 2 IEQs, while one with a diameter of 75 μm is 0.5 IEQ. Litex agarose possesses the following properties: a gel strength ≥1000 g/cm$^2$ at a 1.5% gel *and a viscosity* of from 5.8 to 8.7 cP when a 1.5% solution was used, a gelling temperature of 40-43° C. for a 1.5% solution, an EEO (electro endosmosis) value of from 0.06 to 0.12, and sulphate content ≤0.30%. The solutions were prepared in minimal essential medium plus 25 mM HEPES.

Suspensions were expelled beneath the surface of sterile mineral oil, to yield four, 0.125 ml spherical beads, approximately 5-6 mm in diameter, each of which contained 500 IEQ.

These, uncoated agarose beads were cultured at 37° C., in a humidified, 5% $CO_2$ atmosphere. After 5-7 days, a second coat of 5%, SG agarose was applied, yielding agarose coated, islet containing agarose beads, with a final diameter of 8-9 mm.

These beads were cultured at 37° C. in a humidified 5% $CO_2$ atmosphere until used in experiments which follow. They were placed in a culture medium (11 mM glucose, supplemented with 2.5% heat inactivated porcine serum, and 1% antibiotic/antismycotic). The culture medium was changed weekly, and samples of media were analyzed, 24 hours after change, every week, for assays discussed infra.

Example 6

Figure 6:
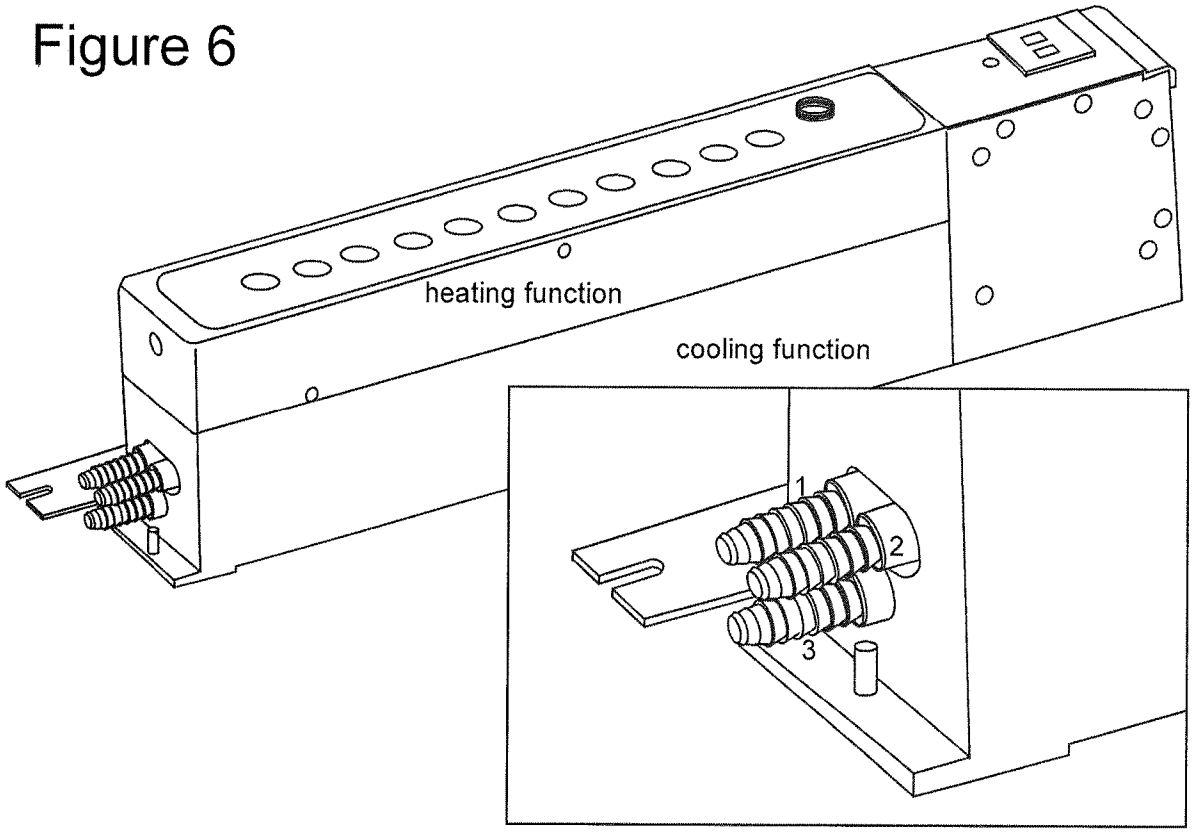
FIG. 6 shows a device used to maintain temperature gradient in operation of the invention.
Figure 7:
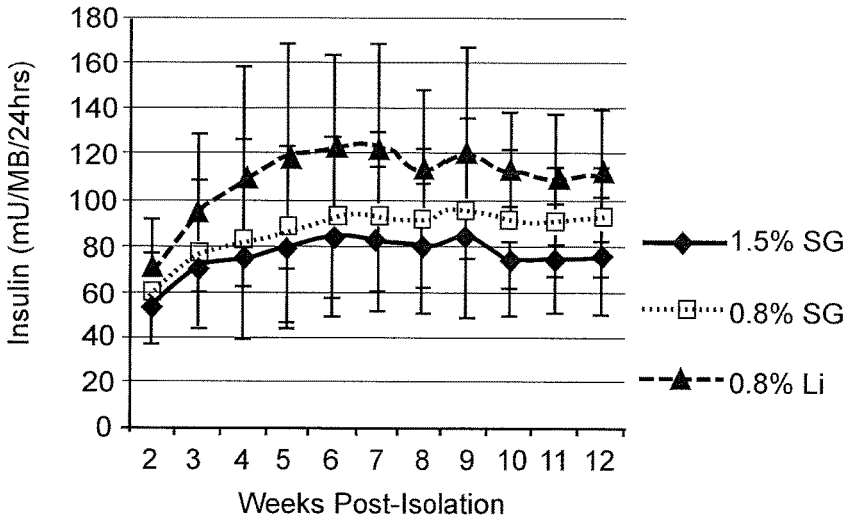
FIG. 7 depicts levels of insulin production from beads made with different concentrations and types of agarose.

As noted in the prior example, culture media samples were taken from the samples, and assayed for insulin content, using a commercially available porcine insulin ELISA. The results are depicted in FIG. 6. It will be seen that islets encapsulated in 0.8% Li outperformed both islets encapsulated in 0.8% SG, and 1.5% SG with respect to insulin production.

Example 7

The in vitro experiments presented supra were extended to in vivo experiments, as discussed herein.

Adult (8 week old rats) were used in these experiments. Animals were divided into groups of "insulin only" controls, or bead recipients. All animals received 65 mg/kg of streptozotocin via tail vein injection to induce diabetes.

Presence of diabetes was confirmed by assaying blood of subject animals for non-fasting glucose levels. A level over 400 mg/dL of glucose for 3 consecutive days was taken to indicate diabetes was present. Any animals which did not exhibit diabetes within 2 weeks received a second dose of streptozotocin, after which all animals became diabetic.

The animals chosen for receiving implants received the beads in accordance with Gazda, et al., Cell Transplant, 16:609-620 (2007), which is incorporated by reference in its entirety. To elaborate, 12-13 week old animals were anesthetized, using isoflurane. Following a midline incision along the peritoneal cavity, beads were placed therein.

The number of beads placed in each animal varied, depending upon the highest dose of insulin given to the particular animal over the 3 day period prior to the implant, divided by the average insulin production per macrobead (based upon the insulin produced by the beads over the 4 week period prior to implantation). Mice received the amount of beads necessary to provide the exact insulin dose they had received prior to implantation (1×), or 1.7× that dose. Female and male animals received beads equal to 1×, but only males received 1.7×, in part because male rats weight more than female rats.

There were no significant differences seen in pre-implant insulin requirements with respect to the different implant types (1.5% SG, 0.8% SG, 0.8% Li); however, more macrobeads were required for 1.5% SG beads, and the fewest were required for 0.8% Li.

Following implantation, the animals were maintained for 90 days, with blood glucose and body weight being monitored regularly.

Female mice (all in the 1× group) showed an immediate, sustained normalization of blood glucose levels as compared to mice receiving insulin controls. Male rats in the 1× group, exhibited an immediate, but temporary, improvement in blood glucose regulation, which returned to pre-implant levels by about 30 days post-implant.

Example 8

Studies were carried out on the macrobeads after the recipient animals were sacrificed and examined for structural integrity and functional capacity.

Gross examination showed that, only two of 1540 macrobeads recovered showed any structural damage.

The foregoing examples describe various features of the invention, which relate to secretory cell-containing agarose macrobeads, coated with agarose, where the agarose used for the macrobeads had the properties of Litex agarose, set forth supra.

As set forth herein, the term "macrobead" refers to a structure that is essentially spherical, with a diameter of from about 4 to about 10-12 mm in diameter, most preferably from about 6 to about 8 mm in diameter. The second agarose layer is preferably from about 0.05 to about 5 mm in thickness, most preferably from about 0.5 mm to about 5 mm in thickness, even more preferably, from about 1.0 mm to about 3 mm, and most preferably, from about 1.0 mm to about 2.0 mm in thickness. The second agarose layer may, but need not be, the same agarose used to make the bead.

"Macrobeads" is used as a preferred structure; however, any solid, agarose structure which encapsulates secretory cells, and is preferably coated with a second, agarose layer, are features of the invention.

The secretory cells may vary. Any cell or organelle which yields a desirable, secretory product may be encapsulated. Islets, cancer cells, and stem cells are exemplary of the types of materials which can be used. Each bead may contain a varying number of cellular organelles, for islets, for example, from about 50 to about 5000 islet equivalents ("IEQs" hereafter), more preferably, from about 100 to about 2500 IEQs, even more preferably, from about 250 to about 1000, and most preferably, from about 475 to about 550 IEQs. About 500 IEQs is most especially preferred.

Also a feature of the invention is an improved method for making macrobeads, regardless of the agarose used. Cells are mixed with agarose, and then formed into a suspension which is in turn used to forma bead. The bead, e.g., a macrobead, is then coated with agarose, after which the resulting coated bead is dispensed into a sample of mineral oil at a temperature gradient, such that the bead contacts mineral oil at a higher temperature and drops to oil at a lower temperature. The beads may contain any cell type desired such as, but not being limited to secretory cells, cancer cells, islets, stem cells, such as pluripotent stem cells, and so forth In particularly preferred embodiments, "trumpet" and "straw" tools, as described herein, are used to remove the uncoated, and the coated beads, respectively.

The temperature gradient of the mineral oil can vary. Preferably, the gradient is from 20° C. to 50° C., i.e., the difference between the highest and lowest temperatures falls within this range. More preferably, the difference is from 20° C. to 35° C.

The highest temperature of the oil may vary, but is preferably between 20° C. and 30° C., more preferably between 20° C. and 35° C. Similarly, the lowest temperature may vary, and run from 0° C. to −8° C., and more preferably, from 0° C. to −2° C.

Other aspects of the invention will be clear to the skilled artisan, and need not be elaborated further.

The terms and expressions which have been employed are used as terms of description and not of limitation, and there is no intention in the use of such terms and expression of excluding any equivalents of the features shown and described or portions thereof, it being recognized that various modifications are possible within the scope of the invention.

We claims:

1. A method for producing a composition of matter comprising a sample of live cells in an agarose containing bead, wherein said bead is coated with agarose, comprising:

(a) mixing a first sample of agarose with said sample of live cells to form a suspension;

(b) moving said suspension to a first sample of mineral oil, to form a bead from said suspension;

(c) removing said bead from said first sample of mineral oil;

(d) rinsing mineral oil from said bead;

(e) moving said bead with a trumpet tool to a second solution of agarose;

(f) coating said bead with said second solution of agarose, (g) removing said bead from said second solution of agarose with a straw tool, and (h) dispensing said coated bead into a second sample of mineral oil, wherein said sample of mineral oil is kept at a temperature gradient so that said bead moves along a path from a location in the mineral oil that is at a higher temperature of about 20° C. to about 30° C. to a location in the mineral oil at a lower temperature of about 0° C. to about −8° C.

2. The method of claim 1, wherein said cells are secretory cells.

3. The method of claim 1, wherein said cells are cancer cells.

4. The method of claim 1, wherein said cells are cancer stem cells.

5. The method of claim 1, wherein said cells are islet cells.

6. The method of claim 1, wherein said cells are stem cells.

7. The method of claim 6, wherein said cells are embryonic stem cells.

8. The method of claim 1, wherein said cells are pluripotent cells.

9. The method of claim 1, further comprising removing said bead from said first or second sample of mineral oil with a trumpet tool.

10. The method of claim 1, wherein said higher temperature is from about 20° C. to about 25° C. and said lower temperature is from about 0° C. to about −2° C.

*11. The method of claim 1, wherein said first sample of agarose has a gel strength of ≥1000 g/cm$^2$ at a 1.5% gel, and a viscosity of from 5.8 to 8.7 cP, a gelling temperature of 40-43° C. for a 1.5% solution, an electro endosmosis value of from 0.0 to 0.12, and a sulphate content ≤0.30%.*

*12. The method of claim 1, wherein said second sample of agarose has a gel strength of ≥1000 g/cm$^2$ at a 1.5% gel, and a viscosity of from 5.8 to 8.7 cP, a gelling temperature of 40-43° C. for a 1.5% solution, an electroendosmosis value of from 0.0 to 0.12, and a sulphate content ≤0.30%.*

*13. The method of claim 1, wherein said first and second samples of agarose have a gel strength of ≥1000 g/cm$^2$ at a 1.5% gel, and a viscosity of from 5.8 to 8.7 cP, a gelling temperature of 40-43° C. for a 1.5% solution, an electroendosmosis value of from 0.0 to 0.12, and a sulphate content ≤0.30%.*

*14. The method of claim 1, wherein said live cells are cancer cells.*

*15. The method of claim 14, wherein said cancer cells are renal cancer cells.*

*16. The method of claim 11, wherein said live cells are islets.*

*17. The method of claim 11, wherein said live cells are stem cells.*

* * * * *